United States Patent
Luck et al.

(10) Patent No.: US 9,493,381 B2
(45) Date of Patent: Nov. 15, 2016

(54) CATALYTIC PROCESS FOR THE CONVERSION OF A SYNTHESIS GAS TO HYDROCARBONS

(75) Inventors: Francis Luck, Noisy-le-grand (FR); Charlotte Pham, Strasbourg (FR);
(Continued)

(73) Assignees: SICAT LLC, New York, NY (US); TOTAL S.A., Courbevoie (FR);
(Continued)

(*) Notice: Subject to any disclaimer, the term of this patent is extended or adjusted under 35 U.S.C. 154(b) by 0 days.

(21) Appl. No.: 14/123,235

(22) PCT Filed: May 31, 2012

(86) PCT No.: PCT/FR2012/051224
§ 371 (c)(1),
(2), (4) Date: Mar. 20, 2014

(87) PCT Pub. No.: WO2012/164231
PCT Pub. Date: Dec. 6, 2012

(65) Prior Publication Data
US 2014/0194542 A1    Jul. 10, 2014

(30) Foreign Application Priority Data

Jun. 1, 2011    (FR) ...................................... 11 01704
Aug. 2, 2011    (FR) ...................................... 11 57096

(51) Int. Cl.
*C07C 1/04*    (2006.01)
*C10G 2/00*    (2006.01)
(Continued)

(52) U.S. Cl.
CPC ................ *C07C 1/044* (2013.01); *B01J 21/06* (2013.01); *B01J 23/745* (2013.01); *B01J 23/75* (2013.01);
(Continued)

(58) Field of Classification Search
CPC ............ C10G 2/33; C10G 2/331; C10G 3/332
(Continued)

(56) References Cited

U.S. PATENT DOCUMENTS

| 5,648,312 A | 7/1997 | Rivas et al. |
|---|---|---|
| 2005/0002838 A1 | 1/2005 | Mogensen |
| 2006/0133977 A1* | 6/2006 | Male et al. ................ 423/239.1 |

FOREIGN PATENT DOCUMENTS

| EP | 1985361 A1 | 10/2008 |
|---|---|---|
| EP | 2314557 A1 * | 4/2011 |

(Continued)

OTHER PUBLICATIONS

Osa, et al. "Influence of the catalytic support on the industrial Fischer-Tropsch synthetic diesel production" Catalysis Today 2011, 176, pp. 298-302.*

(Continued)

*Primary Examiner* — Jafar Parsa
*Assistant Examiner* — Medhanit Bahta
(74) *Attorney, Agent, or Firm* — Ladas & Parry LLP

(57) ABSTRACT

Catalytic process for the partial conversion of a gaseous mixture containing carbon monoxide and hydrogen into a mixture of hydrocarbons, including bringing the said gaseous mixture into contact with a solid catalyst, the solid catalyst having a porous support with a composite material including SiC and a titanium carbide and/or a titanium oxide, and an active phase. The support is prepared in the form of grains, beads, or extrudates, or in the form of cylinders or sheets of cellular foam.

24 Claims, 2 Drawing Sheets

(75) Inventors: Patrick Nguyen, Strasbourg (FR);
Cuong Pham-Huu, Strasbourg (FR);
Benoit De Tymowski, Strasbourg (FR)

(73) Assignees: CENTRE NATIONAL DE LA RECHERCHE SCIENTIFIQUE, Paris (FR); UNIVERSITE DE STRASBOURG, Strasbourg (FR)

(51) Int. Cl.
| | |
|---|---|
| *B01J 27/224* | (2006.01) |
| *B01J 21/06* | (2006.01) |
| *B01J 27/22* | (2006.01) |
| *B01J 37/02* | (2006.01) |
| *B01J 23/745* | (2006.01) |
| *B01J 23/75* | (2006.01) |
| *B01J 23/78* | (2006.01) |
| *B01J 23/83* | (2006.01) |
| *B01J 23/89* | (2006.01) |
| *B01J 35/00* | (2006.01) |
| *B01J 35/10* | (2006.01) |
| *B01J 37/00* | (2006.01) |

(52) U.S. Cl.
CPC .............. *B01J 23/78* (2013.01); *B01J 23/83* (2013.01); *B01J 23/8906* (2013.01); *B01J 23/8913* (2013.01); *B01J 27/22* (2013.01); *B01J 27/224* (2013.01); *B01J 35/002* (2013.01); *B01J 35/1009* (2013.01); *B01J 35/1038* (2013.01); *B01J 35/1061* (2013.01); *B01J 35/1066* (2013.01); *B01J 37/0009* (2013.01); *B01J 37/0201* (2013.01); *C07C 1/0435* (2013.01); *C10G 2/332* (2013.01); *C10G 2300/1022* (2013.01); *C10G 2300/703* (2013.01)

(58) Field of Classification Search
USPC .................................................. 518/719, 721
See application file for complete search history.

(56) References Cited

FOREIGN PATENT DOCUMENTS

| WO | WO 2008104793 A2 * | 9/2008 |
| WO | WO2010049715 A1 * | 5/2010 |
| WO | WO 2011028466 A2 * | 3/2011 |
| WO | WO 2012032325 A1 * | 3/2012 |

OTHER PUBLICATIONS

Nguyen, P. et al. Appl. Cat. A: General 2001, 391, pp. 443-454.*
International Search Report mailed Aug. 6, 2012, corresponding to PCT/FR2012/051224.
Enrique Iglesia et al., Selectivity Control and Catalyst Design in the Fischer—Tropsch Synthesis: Sites, Pellets, and Reactors, Advances in Catalysis, vol. 39, p. 221-302.
Shreyas Rane et al., Effect of alumina phases on hydrocarbon selectivity in Fischer—Tropsch synthesis, Applied Catalysis A: General, vol. 388 (2010) 160-167.
Solvi Storsaeter et al., Characterization of alumina-, silica-, and titania-supported cobalt Fischer-Tropsch catalysts, Journal of Catalysis, vol. 236 (2005), 139-152.
Oyvind Borg et al., Fischer-Tropsch synthesis: Cobalt particle size and support effects on intrinsic activity and product distribution, Journal of Catalysis, vol. 259 (2008) 161-164.

* cited by examiner

CATALYTIC PROCESS FOR THE CONVERSION OF A SYNTHESIS GAS TO HYDROCARBONS

This application is a 371 of PCT/FR2012/051224, filed on May 31, 2012, which claims priority to French Application No. 1101704, filed Jun. 1, 2011, and French Application No. 1157096, filed Aug. 2, 2011.

TECHNICAL FIELD OF THE INVENTION

This invention relates to the Fischer-Tropsch synthesis, and more specifically the catalysts for this reaction. It relates to a new catalyst that includes cobalt deposited on a SiC/TiC and/or SiC/TiO$_2$ support with a high specific surface area and a preparation process for said catalyst.

PRIOR ART

The Fischer-Tropsch synthesis (also referred to here as "FTS"), invented in 1923, transforms a mixture of carbon monoxide (CO) and hydrogen (H$_2$) called "synthesis gas", obtained from carbonaceous raw materials (in particular coal), in a mixture of gaseous and liquid hydrocarbons. The reaction is exothermic and occurs in the presence of a catalyst. For some time, there has been renewed interest in this process. There are multiple reasons: the high cost of crude oil, legislative restrictions on fuels and emissions produced by the combustion thereof, geopolitical considerations aimed at reducing energy dependency (in particular in the United States, which has the largest reserve of coal in the world), the increasing energy needs of China and India (two countries that have few oil resources, but enormous coal resources), the possibility of using biomass (the only inexhaustible carbonaceous resource) for FTS.

Thus, a large amount of research has been conducted on the geometry of the reactor, on the catalyst and on reaction conditions. In particular, the catalyst was the subject of much research, for the composition and microscopic structure of the active phase as well as for the catalyst support.

In general, there are two large families of processes, exploiting two different types of catalysts, which have been used for FTS: slurry-type processes (using a cobalt- or iron-based catalyst) and fixed bed processes (most of which use a cobalt-based catalyst).

The catalyst for FTS must successively break bonds (dissociation of CO and H$_2$), then reform others from them (hydrogenation and chain growth by C—C coupling at the surface of the metal). It is known that the metals enabling the best dissociation and the best coupling are those of group 8 (Co, Fe and Ru) as well as Ni. The choice of the metal is a determining factor both for the selectivity and for the price of the catalyst.

It is known that iron-based catalysts form a large amount of CO$_2$ via the reaction called "water gas shift" (CO+H$_2$O↔CO$_2$+H$_2$). Such catalysts are not suitable for GTL ("gas to liquids") but rather for synthesis gases resulting from the gasification of coal or biomass ("coal to liquids", "biomass to liquids", low H$_2$/CO ratio). In addition, these catalysts produce linear olefins as well as alcohols, aldehydes and ketones. Ruthenium is the most active but also the most expensive. Therefore, cobalt, which has the best equilibrium between stability, activity and cost, is primarily used.

The known cobalt-based catalysts generally include an active phase including between 10 and 30% by mass of cobalt, a second metal as a promoter (typically Pt, Ru or Pd) and a structural dopant (typically Zr, Ba, La), deposited on a refractory oxide-based support with a high specific surface area (often modified by a structural dopant). It is known that the size of the Co particles is a determining factor for the activity and selectivity of the FT catalyst. Below 8 nm, the activity and selectivity decrease significantly, and the optimal size of the cobalt particles appears to be around 8 to 10 nm.

Cobalt must be in its metallic form, and therefore the reduction of its oxide must be complete. However, on oxide-based supports (typically SiO$_2$, Al$_2$O$_3$, TiO$_2$ or a combination of the latter), the small Co particles are difficult to reduce because of the strong metal/support interaction. For this reason, a promoter (typically Ru, Pt, Pd) is associated with the active phase in order to promote its reduction. These noble metals are known to form bimetallic particles and alloys that influence the selectivity and activity and the dispersion of Co; moreover, they inhibit deactivation. However, an excessive amount of promoter may block the active sites of the Co. The addition of zirconium to an alumina-based catalyst support promotes the reduction of cobalt oxides deposited on said support; the Zr limits the formation of aluminates. The cobalt particles must be suitably dispersed on the support. If the dispersion of particles is poor, the active sites of the cobalt are not optimally used. However, a good dispersion of the cobalt particles leads to an increase in the catalytic conversion of carbon monoxide.

In general, the catalyst support plays a very important role in FTS. Functionally, it must be capable of dispersing the Co particles, have a very good mechanical resistance (in particular in "slurry" mode), and provide thermal stability to the Co particles.

Moreover, the support must be resistant to hydrothermal conditions as well as the acids and alcohols formed during the Fischer-Tropsch synthesis. However, alumina and titanium dioxide and silica do not show high stability in the presence of high partial pressures of water, alcohol and acids formed by FTS. Such supports must therefore be stabilized in order to overcome solubility problems.

U.S. Pat. No. 6,875,720 discloses the improvement of the resistance of alumina by protection with silicon, zirconium and titanium; a titanium dioxide-based support (reference P25 ex-Degussa), after transformation into rutile and forming by atomization, is protected by adding Si.

Patent application US 2005/0124490 describes the use of alumina promoted with silica in order to increase its resistance to acids and alcohols. U.S. Pat. No. 7,163,963 describes the doping of an alumina with rare earth elements (in particular La or Nd) in order to increase the chemical resistance of the support.

Alumina- and silica-based supports are most commonly used, although a TiO$_2$-based support also has excellent performance. It is normally accepted by a person skilled in the art that shaped TiO$_2$ (in particular in the form of pellets by extrusion, or microspheres by atomization) has a lower mechanical resistance than do the aforementioned oxide supports. U.S. Pat. No. 5,484,757 describes a process for producing TiO$_2$ catalyst supports with improved mechanical strength.

In the article published in *Journal of Catalysis* 236 (2005) 139-152, it was demonstrated that cobalt-based catalysts and rhenium-promoted cobalt deposited on rutile TiO$_2$ with a small specific surface area having macropores (diameter 790 nm) were more selective than the homologs prepared on γ-alumina and silica. The authors noted that the porous distribution of the support has a major influence on the size and the morphology of the cobalt particles.

To subtract the influence of the chemical nature of the support, the same research team studied the influence of the size of the pores of different alumina supports on $C_{5+}$ selectivity (i.e. the selectivity to hydrocarbons having at least 5 carbon atoms). It was clearly demonstrated that the larger the mean diameter of the pores is, the better its $C_{5+}$ selectivity will be.

In the article *Journal of Catalysis* 259 (2008) 161-164, the authors did away with the size of the cobalt particles and synthesized a plurality of series of catalysts prepared on $\gamma$-$Al_2O_3$ and $\alpha$-$Al_2O_3$. The catalysts prepared on alpha alumina were found to be systematically more selective than their homologs prepared on gamma alumina. In the article *Applied Catalysis A: General* 154 (2010) 162-182, the authors observed the influence of the crystallographic phase of the same alumina but having undergone heat treatments at different temperatures. The larger the pore size is, the more the $C_{5+}$ selectivity is improved. The catalysts prepared on alpha alumina with a low porous volume and a small specific surface area were found to be more selective than their homologs prepared on gamma alumina.

In the U.S. Pat. No. 7,351,679, a $\gamma$-alumina was heat-treated so as to have at least 10% by mass of $\alpha$-alumina and a specific surface area smaller than 50 $m^2/g$. This document refers to the article "*Selectivity control and catalyst design in the Fischer-Tropsch synthesis: sites, pellets and reactors*" published in Advances in Catalysis, Vol. 39, 1993, pages 221-302, which describes that a maximum $C_{5+}$ selectivity is reached by designing a support (or catalyst pellet) having an optimal diffusion of reagents/products. In effect, in large pores, the alpha-olefins will have a tendency to desorb before extending their carbon chain. In narrow pores, the CO diffusion will be slowed, leading to a deficiency of CO in the catalyst particles and an enrichment of hydrogen. This enrichment will lead to hydrogenation of the olefins, reducing the selectivity of heavier hydrocarbons.

A parameter $\chi$, a function of the particle size, the porosity, the cobalt load and the cobalt dispersion, was introduced in order to express the diffusion resistance in a catalyst particle; it is defined by:

$$\chi = R_o^2 \phi \Theta / r_p$$

with:
$R_o$: diameter of the catalyst particle (m)
$\phi$: porosity of the catalyst
$\Theta$: density of the catalytic sites (site/$m^2$)
$r_p$: mean radius of the pores (m)

The optimum $C_{5+}$ selectivity is given for a value of $\chi$ between 500 and 1000×1016 $m^{-1}$. To vary $\chi$, the most sensitive parameter is the macroscopic size of the catalyst pellet. In a fixed bed, the catalyst must have a size greater than a millimeter in order to limit head loss. In a fluidized bed, the value of $\chi$ is lower than the optimum because it is not possible to independently vary the cobalt dispersion, the porous volume and the cobalt load.

The aforementioned document U.S. Pat. No. 7,351,679 proposes a cobalt catalyst on alumina with a low specific surface area (<50 $m^2/g$) having large pores. Such an alumina can be obtained by heat-treating a gamma alumina between 700 and 1300° C. for 1 to 15 hours. Ideally, the support must contain at least 80% alpha alumina and a specific surface smaller than 30 $m^2/g$. Such a support makes it possible to synthesize a catalyst for the Fischer-Tropsch reaction with a higher $C_{5+}$ selectivity. However, the small specific surface area of the support does not enable a large amount of cobalt to be deposited, and the inventors are limited to 12% by mass of cobalt so as not to affect the $C_{5+}$ selectivity.

A person skilled in the art is therefore faced with an equilibrium between the specific surface area, the pore diameter and the porous volume: the more alpha alumina that the material contains, the smaller its specific surface area will be and the larger the size of the pores will be; conversely, the more gamma alumina phase that the material contains, the larger its specific surface area will be, but the narrower the pores will be. A large specific surface area enables better dispersion of the cobalt, which results in better activity (conversion of carbon monoxide) and large pores lead to an increase in $C_{5+}$ selectivity.

There is therefore a need to have a support capable of resisting the drastic hydrothermal conditions of the Fischer-Tropsch synthesis, having a specific surface area large enough to disperse the active phase and large pores so as to improve the $C_{5+}$ selectivity.

Moreover, there is also a need to have a $TiO_2$-based support, known to a person skilled in the art for improving the $C_{5+}$ selectivity, and which is mechanically stable enough to be used in the Fischer-Tropsch reaction.

Another problem with Fischer-Tropsch catalysts is associated with their mechanical resistance. In effect, one of the requirements of a Fischer-Tropsch catalyst used in a fluidized bed reactor is that the catalyst pellets must maintain their integrity for as long as possible. In effect, one of the causes of a shorter lifetime of Fischer-Tropsch catalysts is the loss of active cobalt by attrition. Furthermore, the reaction products may be polluted by fine catalyst powders formed by their mechanical degradation. Although they have very good results in particular with regard to $C_{5+}$ selectivity, $TiO_2$ supports are not envisaged in a fluidized bed due to the lack of resistance to attrition. Silica does not appear to be satisfactory, and only modified alumina can withstand the constraints of the process. As mentioned above, there is no material, however, that has both a large specific surface area, i.e. at least greater than 30 $m^2/g$ and preferably greater than 50 $m^2/g$ having, in addition to large pores (greater than 30 nm), and acceptable mechanical resistance. In addition, in consideration of the promising results obtained with FTS catalysts on a $TiO_2$ support, more specifically concerning the $C_{5+}$ selectivity, it would be advantageous to have a catalyst support with a chemical surface identical or similar to that of the $TiO_2$, preferably with a specific surface greater than 30 $m^2/g$ and in particular mechanical properties enabling the catalyst to be used in a fixed bed reactor and in a fluidized bed reactor.

Objectives of the Invention

The objective of this invention is to provide a catalyst for the Fischer-Tropsch reaction that is extremely active, with a high $C_{5+}$ selectivity.

Another objective of this invention is to provide a catalyst support, which can be used in particular for the Fischer-Tropsch reaction, having high mechanical robustness in order to enable its use in a fluidized bed, reputed to cause significant damage to the catalyst particles.

Finally, another objective of the invention is to provide a catalyst that offers the possibility of facilitating the recovery of the active phase and the dopant elements of the catalysts used.

In the present invention, the inventors provide a solution to the stated problems by proposing a carbide-based material enabling the specific surface area, the macroporous volume and the macroporous distribution to be modified practically independently. This type of material is particularly suitable for producing a catalyst for the Fischer-Tropsch reaction, which may be used both in a fluidized bed and in a fixed bed. According to the invention, this type of material contains at least one silicon carbide phase (SiC), the preferred phase for silicon carbide being the beta phase, and at least one phase comprising titanium in the form of titanium carbide (TiC) and/or titanium oxide ($TiO_2$).

This type of material can be subjected to an oxidizing heat treatment that leads to partial or total oxidation of the carbides, and more specifically of the TiC into $TiO_2$, the latter being capable of being in anatase form, or in rutile form, or in the form of a mixture of the two, or in an amorphous form.

Such a material is suitable for the synthesis of cobalt-, iron- or ruthenium- or nickel-based catalysts. It is possible to add metals of groups 7, 8, 9 and 10. A cobalt-based catalyst prepared on this new support also makes it possible to increase the activity while keeping a very high $C_{5+}$ selectivity.

Finally, such a material makes it possible to produce an economically advantageous catalyst for the Fischer-Tropsch reaction because the recycling capacity of the metals and the support is greater than that known to a person skilled in the art.

A first objective of the invention is therefore a process of at least partial catalytic conversion of a gaseous mixture containing CO and $H_2$ in a mixture of hydrocarbons, comprising a step of placing said gaseous mixture in contact with a solid catalyst, said solid catalyst comprising:
  a porous support comprising a composite material comprising SiC and a titanium carbide (composite called "SiC/TiC") and/or a titanium oxide (composite called "SiC/$TiO_2$"), and
  an active phase.

Said support may in particular be in the form of pellets, beads, extruded or in the form of a cellular foam, and in the last case in particular in the form of plates or cylinders.

In one embodiment, said active phase includes primarily cobalt or iron, and optionally the other of the metals, and optionally one or more transition metals of groups 7, 8, 9 and/or 10. It may also include a promoter, preferably at a content not exceeding 2% by mass. Said promoter may be selected from the group formed by: ruthenium (preferred promoter), platinum, rhenium, rhodium, iridium, palladium, rare earth elements and oxides thereof, alkaline earth elements and oxides thereof.

In another embodiment, which may be combined with the others, said porous support has a specific BET surface area greater than 5 $m^2/g$, preferably greater than 30 $m^2/g$, more preferably greater than 40 $m^2/g$, and even more preferably greater than 60 $m^2/g$.

In another embodiment, which may also be combined with the others, said porous support has a microporous surface area greater than 10 $m^2/g$, and preferably greater than 20 $m^2/g$. Advantageously, its porous volume, developed in pores with diameters of between 30 nm and 300 nm, and measured by mercury intrusion, is greater than 0.12 $cm^3/g$, preferably greater than 0.15 $cm^3/g$ and even more preferably greater than 0.20 $cm^3/g$.

A particular aspect of the invention is the production and use of a catalyst for the Fischer-Tropsch synthesis, which includes cobalt deposited on a mixed support comprising, on the one hand, β-SiC and, on the other hand, TiC and/or $TiO_2$, said support having at least one specific surface area greater than 30 $m^2/g$, preferably greater than 40 $m^2/g$, and more specifically greater than 60 $m^2/g$.

The non-oxidized composite comprising SiC and TiC is referred to here as the "composite SiC/TiC", and the composite comprising SiC and $TiO_2$ is referred to as the "composite SiC/$TiO_2$", with the understanding that, unless otherwise indicated and except in a particular context, in the SiC/$TiO_2$ composite, a small portion of the titanium may be present in the form of carbide; the expression "SiC/$TiO_2$/(TiC)" is sometimes used here to designate a compound in which the TiC has been incompletely oxidized into $TiO_2$.

Preferably, the support comprises at least 0.5% of Ti (in particular in its TiC and/or $TiO_2$ form) and preferably more than 1%, these percentages being molar percentages with respect to the sum Ti+Si of the support; they do not take the active phase into account. A molar titanium content of between 0.5% and 15% (and preferably between 1% and 10%) is preferred.

In a particular embodiment, an SiC/$TiO_2$ composite having a specific BET surface area greater than 60 $m^2/g$ and a porous volume, measured by mercury intrusion, greater than 0.12 $cm^3/g$ for pores with a diameter of between 30 nm and 300 nm. This composite can be used as a support for a Fischer-Tropsch synthesis catalyst. Such a composite can be prepared, for example, by depositing an organic source of titanium (i.e. a $TiO_2$ precursor) onto a porous SiC support, without going through the TiC phase. This deposition can take the form of a continuous or non-continuous layer; it is then converted into $TiO_2$.

Preferably, the active phase load (for example, the metal cobalt load) is between 1 and 50% by mass with respect to the total mass of the catalyst (this total mass corresponding to the sum of the masses of the support and the active phase deposited on this support), and more specifically between 5% and 35%, and even more preferably between 5% and 30%.

Advantageously, the catalyst comprises at least one promoter, preferably up to 2% by mass. The promoter can be ruthenium, platinum, rhenium, rhodium, iridium, palladium. Ruthenium is preferred; advantageously, its content does not exceed 2%. The promoter can also be chosen from the rare earth elements, the rare earth oxides, the alkaline earth elements and the oxides thereof, as well as the transition metals and the oxides thereof. As an example, it is possible to use $ZrO_2$ and/or a manganese oxide.

The invention also relates to the use of a catalyst for the Fischer-Tropsch reaction based on cobalt supported on a porous SiC/TiC, SiC/$TiO_2$ or SiC/$TiO_2$/(TiC) composite having a specific surface area greater than 30 $m^2/g$, preferably greater than 40 $m^2/g$ and more specifically greater than 60 $m^2/g$, advantageously with large pores.

Another objective of the invention is to provide a method for preparing a catalyst for the Fischer-Tropsch synthesis that includes a support based on SiC/TiC, SiC/$TiO_2$ or SiC/$TiO_2$/(TiC). This method includes the preparation of a mixture comprising at least one silicon source, at least one carbon source and at least one titanium source and optionally binders and forming agents, this preparation being followed by at least one heat treatment that is intended to transform said silicon source at least partially into silicon carbide and at least part of said titanium source into titanium carbide. Advantageously, this heat treatment is at least partially performed at a temperature of between 1200° C. and 1450° C.

Optionally, an additional oxidation step at a temperature of at least 350° C., and preferably at least 400° C., can be performed in order to partially or totally transform the titanium carbide into titanium dioxide. Such a SiC/$TiO_2$/(TiC) also has excellent mechanical resistance. Its specific surface area can be greater than or equal to 60 $m^2/g$, with large pores.

All of the other preparation techniques capable of leading to a SiC/TiC or SiC/TiO$_2$ composite having the same properties can be used in the context of this invention, such as, for example, a preform containing silicon and/or carbon and/or a carbon precursor on which TiO$_2$ or a titanium precursor is deposited. This technique also makes it possible to concentrate the TiC phase at the surface of the preform after synthesis of the composite.

Yet another objective is a process for preparing and activating a catalyst for use in the catalytic conversion process according to the invention said preparation and activation process including:

(a) at least one step of depositing active phase precursor on a porous support comprising a composite material of the SiC/TiC and/or SiC/TiO$_2$ type;

(b) at least one phase of activating said active phase precursor in order to form the active phase.

Said precursor deposition phase includes at least one phase of impregnating said support with a solution of an active phase precursor, followed by a step of drying and a step of calcination.

Said calcination is advantageously performed at a temperature of between 250° C. and 450° C. for 1 to 14 hours, preferably between 300° C. and 400° C. for 4 to 16 hours.

The invention also relates to the use of the catalyst according to the present invention for the Fischer-Tropsch reaction and which consists of converting a mixture of H$_2$ and CO (syngas or synthesis gas) primarily into C$_{5+}$ hydrocarbons.

FIGURES

FIG. 2 shows a micrograph obtained by scanning electron microscopy of a porous β-SiC/TiC support according to the invention, before impregnation. The acceleration voltage was 3 kV, and the white bar at lower right-hand side indicates the length of 100 μm.

FIG. 3 shows the porous distribution obtained by nitrogen sorptometry for a known porous β-SiC support, for a SiC/TiC support according to the invention, and for a SiC/TiO$_2$ support according to the invention.

FIG. 4 shows the distribution of the porous volume (in cm$^3$/g) obtained by mercury intrusion as a function of the pore diameter (in nanometers) for a known porous β-SiC support and for a TiO$_2$/SiC support according to the invention.

DETAILED DESCRIPTION OF THE INVENTION

In general, in this document, the term "specific surface area" refers to the so-called BET specific surface area, measured by means of the Brunauer—Emmet—Teller method, which is well known to a person skilled in the art.

The "porosity" of a material is normally defined by reference to three categories of pores that are distinguished by their size: microporosity (diameter smaller than 2 nm), mesoporosity (diameter between 2 and 50 nm) and macroporosity (diameter larger than 50 nm); on this topic, see the article of F. Rouquerol et al., "Texture des matériaux pulvérulents ou poreux", published in the collection Techniques de l'Ingénieur, vol. P 1050.

Unless otherwise indicated, all of the percentages that characterize a chemical composition are percentages by mass.

A) Preparation of the Support

Here we will describe a typical mode of preparation of the support. A finely divided silicon source, such as metal silicon (any silicon source may be suitable) in the form of a powder, and at least one source of carbon or carbon precursor, is provided. In one embodiment, this source of carbon or carbon precursor acts as a binder in the production process; it can be a carbonizable resin.

A mixture of the silicon source and the carbon source is formed. A titanium source, such as powder TiO$_2$ (all TiO$_2$ sources may be suitable), is added to this mixture. It is also possible to add porogens to generate meso and/or macropores. The mixture thus obtained is homogenized by the techniques known to a person skilled in the art.

To this mixture, a temporary binder can be added, such as water, polyvinyl alcohol (PVA), polyethyleneglycol (PEG) or any other binder known to a person skilled in the art. Dispersion agents such as dispersants or peptization agents can be added (For example before or after introducing the TiO$_2$ powder into the mixture) in order to better disperse the TiO$_2$ powder. Then, this mixture is formed, for example by atomization and drying of droplets, or by extrusion in order to obtain cylinders, polylobes or other forms. If extrusion is preferred, additives such as plasticizers can be added to confer consistency, which facilitates extrusion, on the mixture. These plasticizers are advantageously carbonizable.

In an alternative of the process, this mixture is infiltrated into a porous foam of a carbonizable polymer (such as a polyurethane foam); this alternative in particular enables cellular foams of SiC/TiC/(TiO$_2$) to be prepared.

After the forming step, the dried precursor is subjected to a heat cycle under an inert atmosphere at a temperature below 1450° C. (preferably below 1400° C.) and for at least one hour. A mixed compound is thus obtained comprising a titanium carbide phase and a beta silicon carbide phase (β-SiC). Optionally, this support can be treated under air at a temperature of between 350° C. and 500° C. for 2 to 10 hours in order to entirely or partially oxidize the TiC into TiO$_2$.

Figure 2:
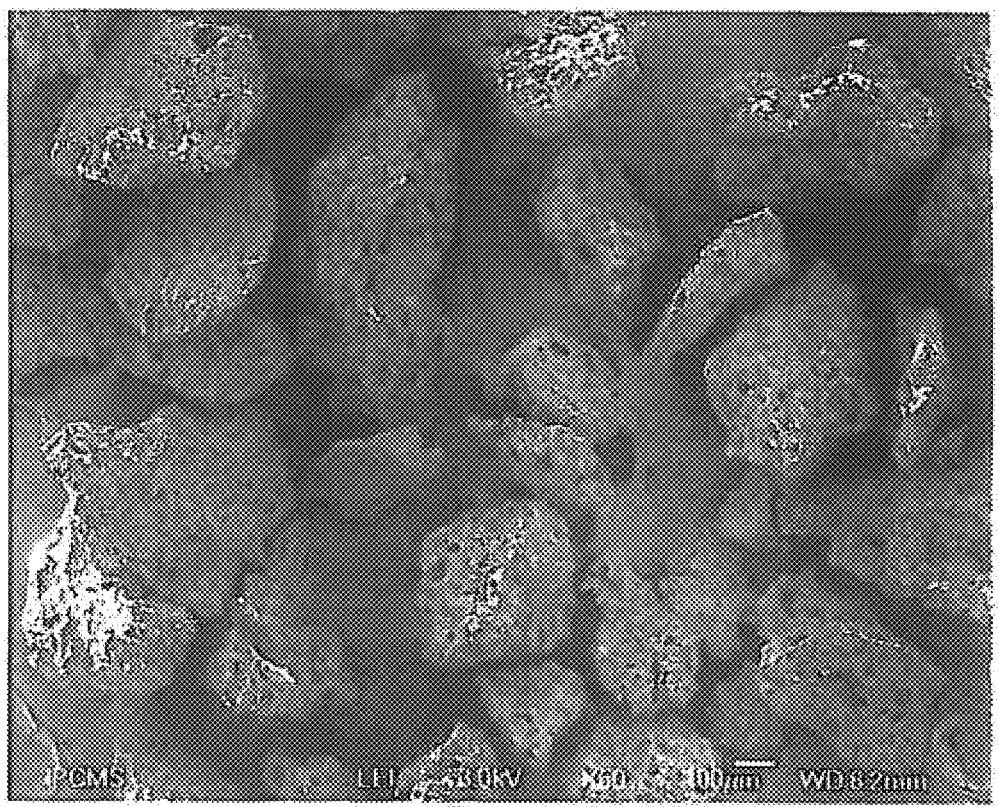
FIGS. 2 to 4 show embodiments of the invention, but without limiting the invention.
Figure 3:
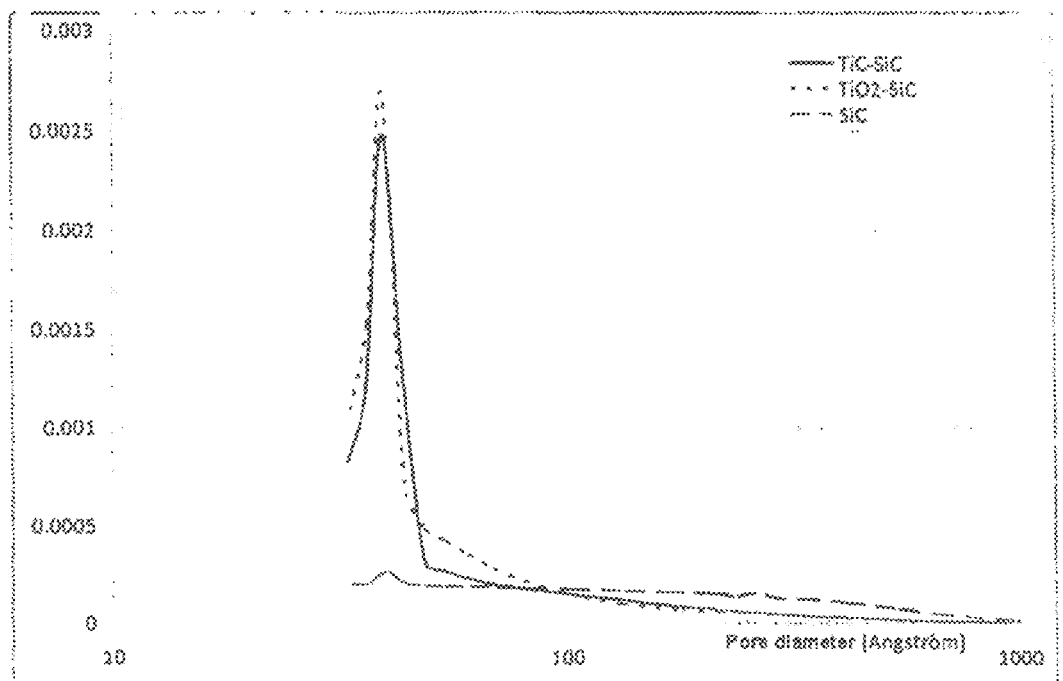
Figure 4:
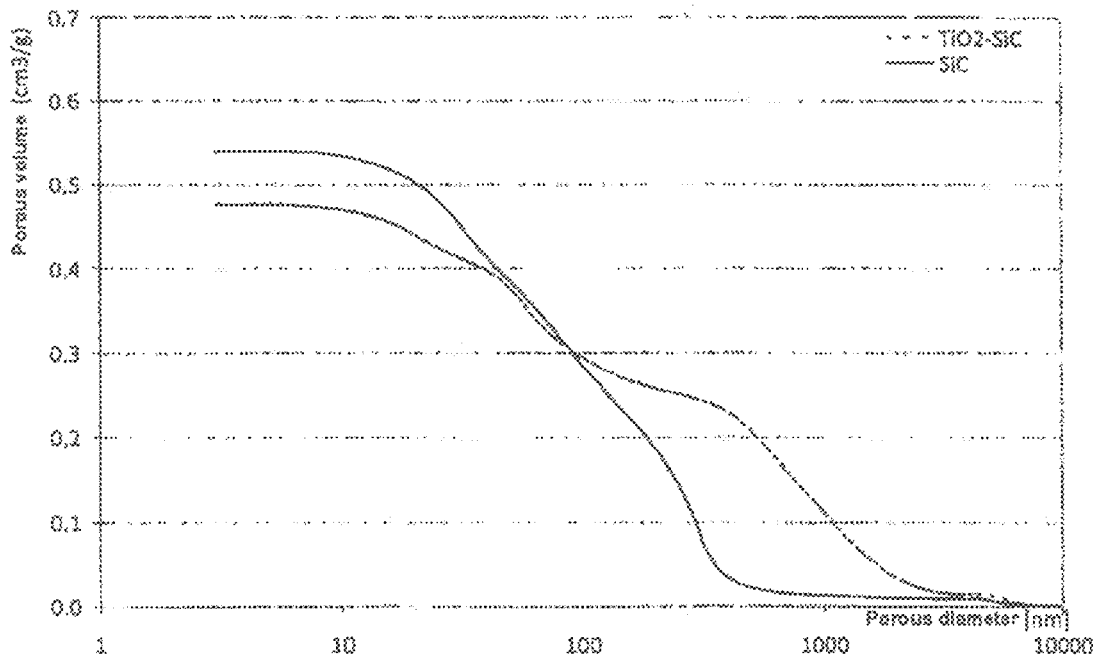

The support according to the invention comprises micro, meso and macropores. FIG. 2 shows an image obtained by scanning electron microscopy of a support according to the invention before impregnation. The macropores are clearly visible and have a porous diameter greater than a micron. FIGS. 3 and 4 characterize the porosity of several typical supports corresponding to the prior art (β-SiC) and to the present invention.

B) Preparation and Activation of the Catalyst

Here we will describe processes for preparing and activating the catalyst. Starting with a catalyst support according to the invention as described above, a catalyst according to the invention can be prepared by any technique known to a person skilled in the art. An advantageous technique of metal and promoter impregnation is that of impregnating the porous volume (incipient wetness impregnation). It consists of dissolving the metals and promoters in a solvent volume approximately equal to the porous volume of the support, and of impregnating the support with this solution.

The preferred cobalt precursor is cobalt nitrate, which is soluble in water and other alcoholic solvents. But other cobalt compounds or salts can also be suitable, for example cobalt acetate, cobalt chloride and cobalt carbonyl.

If it is desired to add a promoter, said promoter can be deposited, for example, by co-impregnation (i.e. one of its soluble salts is introduced into the solution, which comprises the cobalt salt), or by a second impregnation (with a solution of a suitable salt), which follows the step of impregnation of the cobalt.

If a second impregnation is used, it is preferable first to decompose the cobalt salt (preferably nitrate) by a heat treatment, before performing the second impregnation introducing the promoter. However, it is also possible to reduce the cobalt oxide into metal cobalt before performing said second impregnation.

The preferred promoter is ruthenium. Its precursor can be a ruthenium salt capable of being dissolved either in an aqueous solution or in an organic solution. Ruthenium nitrate is preferred; other salts such as ruthenium chloride or ruthenium acetylacetonate can be used.

Among the organic solvents that are suitable, both for the cobalt salt (in particular for the cobalt nitrate) and for the salt of the promoter (and in particular for the ruthenium salt and more specifically for the ruthenium nitrate), acetone, methanol, ethanol, dimethyl formamide, diethyl ether, cyclohexane, xylene and tetrahydrofuran can be mentioned.

After impregnation, the solid is dried at room temperature, typically for 10 hours, then at a higher temperature, advantageously between 100 and 130° C. (typically at 110° C.) for several hours. If organic solvents are used, a slow evaporation with the rotary evaporator is preferred.

The dried catalyst is calcined, preferably under air, at a temperature of between 200° C. and 500° C., preferably between 200° C. and 350° C. In an advantageous embodiment, the temperature increase is at a rate of between 0.5° C./min and 5° C./min. The duration of the treatment can be between 1 and 24 hours and preferably between 2 and 6 hours.

Before it is used, the catalyst must be activated. This can be performed by reduction under a hydrogen flux. This activation can be performed at a temperature of between 250° C. and 450° C., more specifically between 300° C. and 400° C. for 1 to 24 hours and more specifically between and 16 hours. It can be performed in situ in the Fischer-Tropsch reactor. During this reduction, the metal elements (including the promoters), which are found after calcination of their precursors in general in the oxidized state, are reduced into a metal form, finely divided on the porous surface of the support, in order to form the so-called active phase of the catalyst.

C) Use of the Catalyst in the Fischer-Tropsch Synthesis

For the Fischer-Tropsch synthesis, the catalyst according to the invention can be implemented in reactors known to a person skilled in the art for this synthesis, and in particular in a multitubular fixed bed reactor and in a bubbling circulating bed reactor. The catalyst can be used in particular in the form of beads (advantageously microbeads with a diameter of between 20 μm and 400 μm) or extruded or in the form of an alveolar foam.

D) Advantages of the Invention

A first advantage of the support according to the invention is that it makes it possible to considerably increase the activity of the catalyst without altering its $C_{5+}$ selectivity. Another advantage of this support and catalyst is its remarkable mechanical resistance, its hydrothermal resistance and its resistance to chemical attacks. Its high resistance to attrition is particularly advantageous when implementing this support and catalyst in a "slurry"-type reactor. Another advantage of this catalyst is its stability under flux. Finally, another advantage of this catalyst is the possibility of facilitating the recovery of the active phase and the promoter(s) of the catalyst used; in effect, this new support is very resistant to the wet acid or basic treatments that are used to recover the metal elements of the active phase. The SiC/TiC and/or SiC/TiO$_2$ composite makes it possible, owing to its high specific surface area, to better disperse the cobalt particles, thereby increasing the productivity of the catalyst. The presence of mesopores with a diameter greater than around 30 nm and macropores with a diameter greater than 500 nm, or even greater than 1 μm, makes it possible to eliminate diffusion phenomena (or at least significantly reduce the diffusion limitations), thereby leading to an increase in the $C_{5+}$ selectivity.

The catalyst according to the invention is also advantageous for fixed bed processes, because the high mechanical strength of the catalyst pellets makes it possible to limit the formation of fines during loading and unloading of the reactors.

A catalyst prepared on this new type of support also makes it possible to increase the activity, significantly improve the $C_{5+}$ selectivity, and withstand the hydrothermal constraints of the Fischer-Tropsch synthesis.

The inventors noted that the use of the composite according to the invention can make it possible to reduce the load of active phase during the Fischer-Tropsch synthesis. As an example, good results were obtained with a cobalt load on the order of 10% by weight, whereas the processes according to the prior art use catalysts with a cobalt load greater than 30%, which may reach 40% or even 45%.

EXAMPLES

To illustrate the invention and enable a person skilled in the art to carry it out, we will describe some embodiments here, but without limiting the scope of the invention. Example 1 relates to the prior art, examples 2 and 3 relate to the invention. Certain aspects of these examples are illustrated by FIGS. 1 to 4.

In these examples, the specific surface area was determined on the basis of nitrogen adsorption isotherms at variable pressure, and at the temperature of liquid nitrogen, using an automatic Micromeritics Tristar 300™ apparatus. The total specific surface area (called "BET specific surface area") was obtained by the BET method, well known to a person skilled in the art. The external surface area was obtained by the t-plot method. The microporous surface area was obtained by the difference between the total BET specific surface area and the external surface area. The micro and mesoporous distributions were obtained on the basis of the nitrogen desorption isotherm. The meso and macroporous distributions and the total porous volume were obtained by mercury intrusion on an automatic Micrometrics Autopore III™ type 9420 porosimeter.

Example 1

Preparation of the 30% Co Reference Catalyst on a SiC Support

Figure 1:
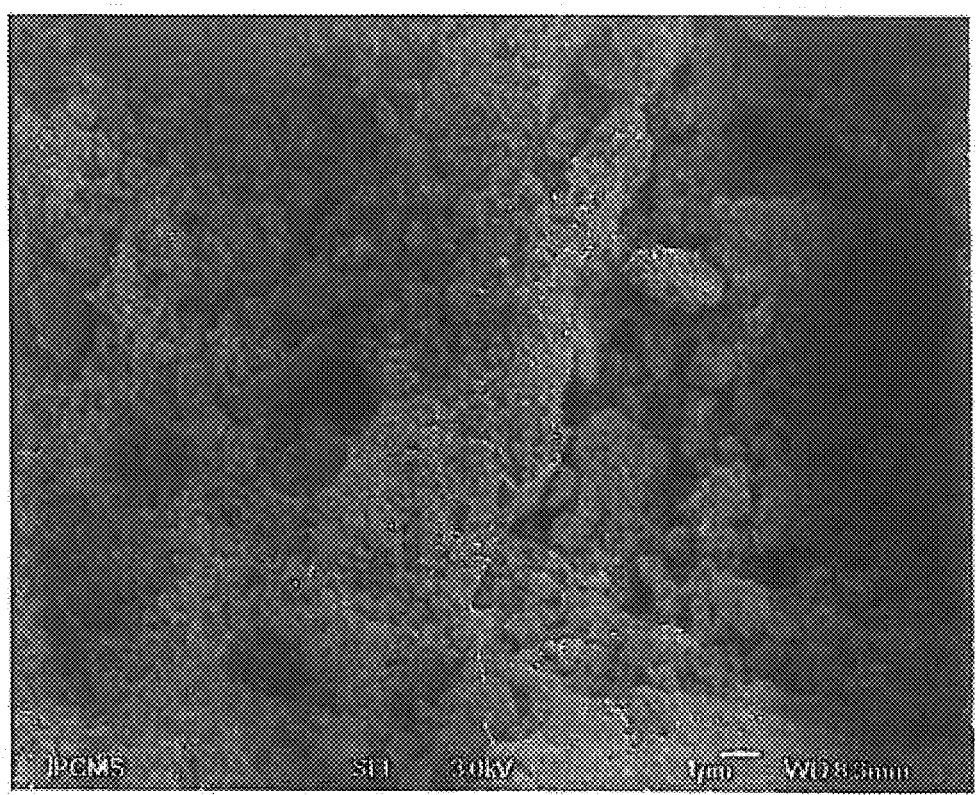
FIG. 1 shows a micrograph obtained by scanning electron microscopy of a sample of a porous β-SiC support according to the prior art, before impregnation. The acceleration voltage was 3 kV, and the white bar at the lower right-hand side indicates the length of 1 μm.

A mass of 20 g of beta silicon carbide (β-SiC) catalyst support with a mean specific surface area (26 m$^2$/g), see FIG. 1, was impregnated with 42.32 g of cobalt nitrate dissolved in 20 g of distilled water. After impregnation, the solid was dried at room temperature for 12 hours, then placed in an oven at 110° C. for 2 hours. Then, the solid was calcined under air at 350° C. for 2 hours. The cobalt oxide thus obtained was reduced under 300 cc/min hydrogen at 300° C.

for 6 hours. The catalyst was passivated at room temperature under a flux containing 1% by volume of $O_2$ diluted in helium.

Example 2

Preparation of a 30% Co Catalyst on a $SiC/TiO_2$ Support According to the Invention A mass of 20 g of $SiC/TiO_2$ catalyst support (see FIG. 2) having a micro, meso and macroporosity and having a specific surface area of 86 m²/g was impregnated with 42.32 g of cobalt nitrate dissolved in 20 g of distilled water. After impregnation, the solid was dried at room temperature for 12 hours, then placed in an oven at 110° C. for 2 hours. Then, the solid was calcined under air at 350° C. for 2 hours. The cobalt oxide thus obtained was reduced under 300 cm²/min hydrogen at 300° C. for 6 hours. The catalyst was passivated at room temperature under a flux containing 1% by volume of $O_2$ diluted in helium.

Example 3

Preparation of a 10% Co Catalyst on a $SiC/TiO_2$ Support According to the Invention A mass of 20 g of $SiC/TiO_2$ catalyst support having a micro, meso and macroporosity and having a specific surface area of 86 m²/g was impregnated with 10.97 g of cobalt nitrate dissolved in 20 g of distilled water. After impregnation, the solid was dried at room temperature for 12 hours, then placed in an oven at 110° C. for 2 hours. Then, the solid was calcined under air at 350° C. for 2 hours. The cobalt oxide thus obtained was reduced under 300 cc/min hydrogen at 300° C. for 6 hours. The catalyst was passivated at room temperature under a flux containing 1% by volume of $O_2$ diluted in helium.

Example 4

Preparation of a 10% Co Catalyst on a SiC/TiC Support According to the Invention A mass of 20 g of TiC/SiC catalyst support having a micro, meso and macroporosity and having a specific surface area of 72 m²/g was impregnated with 10.97 g of cobalt nitrate dissolved in 20 g of distilled water. After impregnation, the solid was dried at room temperature for 12 hours, then placed in an oven at 110° C. for 2 hours. Then, the solid was calcined under air at 350° C. for 2 hours. The cobalt oxide thus obtained was reduced under 300 cc/min hydrogen at 300° C. for 6 hours. The catalyst was passivated at room temperature under a flux containing 1% by volume of $O_2$ diluted in helium.

Example 5

Fischer-Tropsch Synthesis Activity

The catalysts described in examples 1 to 4 were tested in Fischer-Tropsch synthesis. 5 g of catalyst in the form of pellets with a diameter of 250-400 μm were placed in a stainless steel reactor having a diameter of 6 mm. The pressure of the system was increased to 4 MPa (with a ramp of 4 MPa·h⁻¹) under an argon flux. When the desired pressure was reached, the temperature of the reactor was increased to 210° C. (heating ramp of 2 C·min⁻¹). When the desired temperature was reached, the argon flux was replaced by a mixture 50:50 v:v of argon and synthesis gas ($H_2$/CO, 2:1 v:v). The catalyst was activated for 3 days under diluted flux before being subjected to a reaction mixture of pure $H_2$/CO, and the temperature of the reactor could be varied. The activities and selectivities of the catalysts of examples 1 to 4 at different temperatures and spatiotemporal rates are set in tables 1 to 3. The activity of a SiC/TiC-based catalyst is more than twice that of a SiC-based catalyst. The increased activity can be measures in the reactor by a greater increase in temperature for the catalyst according to the invention.

TABLE 1

Activity and selectivity in Fischer-Tropsch synthesis

| | GHSV [h⁻¹] | CO conversion [%] | | $C_{5+}$ [% by mass] | | $g_{C5+}/g_{catalyst}/h$ | |
|---|---|---|---|---|---|---|---|
| | | T = 215° C. | T = 220° C. | T = 215° C. | T = 220° C. | T = 215° C. | T = 220° C. |
| Example 1 (30% Co on SiC) | 1900 | 43.37 | 57.38 | 91 | 90.23 | 0.23 | 0.26 |
| Example 2 (30% Co on SiC/$TiO_2$) | 2750 | 58.78 | 68.23 | 92.42 | 93.08 | 0.41 | 0.48 |

TABLE 2

Activity and selectivity in Fischer-Tropsch synthesis

| | GHSV [h⁻¹] | CO conversion [%] | | $C_{5+}$ [% by mass] | | $g_{C5+}/g_{catalyst}/h$ | |
|---|---|---|---|---|---|---|---|
| | | T = 225° C. | T = 227° C. | T = 225° C. | T = 227° C. | T = 225° C. | T = 227° C. |
| Example 1 (30% Co on SiC) | 1900 | 71.23 | — | 90.28 | — | 0.32 | — |
| Example 2 (30% Co on SiC/$TiO_2$) | 3800 | 58.61 | 62.49 | 92.32 | 90.84 | 0.54 | 0.57 |

TABLE 3

Activity and selectivity in Fischer-Tropsch synthesis

| | GHSV [h$^{-1}$] | CO conversion [%] T = 215° C. | C$_{5+}$ [% by mass] T = 215° C. | g$_{C5+}$/g$_{catalyst}$/h T = 215° C. |
|---|---|---|---|---|
| Example 3 (10% Co on SiC/TiO$_2$) | 2750 | 36 | 93.49 | 0.17 |
| Example 4 (10% Co on SiC/TiC) | 2750 | 53.05 | 91.54 | 0.24 |

TABLE 4

Physical data on the supports

| | Specific BET surface area [m$^2$/g] | Specific surface area due to micropores [m$^2$/g] | External specific surface area [m$^2$/g] | Cumulative porous volume obtained by mercury intrusion [cm$^2$/g] |
|---|---|---|---|---|
| SiC | 25.6 | 1.2 | 24.4 | 0.52 |
| SiC/TiC | 72 | 43 | 29 | 0.43 |
| SiC/TiO$_2$ | 86 | 50 | 36 | 0.43 |

The invention claimed is:

1. A process of at least partial catalytic conversion of a gaseous mixture containing CO and H$_2$ to a mixture of hydrocarbons, comprising a step of placing said gaseous mixture in contact with a solid catalyst, said solid catalyst comprising:
a porous support comprising at least one of a composite material comprising SiC and titanium carbide, and a composite material comprising SiC and titanium oxide, and
an active phase,
wherein said porous support has a molar content of titanium with respect to the molar sum of Si+Ti of between 0.5% and 15%.

2. The process according to claim 1, wherein said composite material has been prepared by a method including the preparation of a mixture comprising at least one silicon source, at least one carbon source and at least one titanium source, this preparation being followed by at least one heat treatment that is intended to transform said silicon source at least partially into silicon carbide and at least part of said titanium source into titanium carbide, said heat treatment being at least partially performed at a temperature of between 1200° C. and 1450° C.

3. The process according to claim 2, wherein said method for preparing said composite material also includes a step of additional oxidation at a temperature of at least 350° C., in order to partially or totally transform the titanium carbide into titanium dioxide.

4. The process according to claim 1, wherein the content of active phase with respect to the total mass of said porous support with its active phase is between 1 and 50% by mass.

5. The process according to claim 1, wherein said active phase includes primarily cobalt or primarily iron.

6. The process according to claim 5,
wherein iron is present in the active phase that includes primarily cobalt; and
wherein cobalt is present in the active phase that includes primarily iron.

7. The process according to claim 5, wherein said active phase further comprises at least one transition metal selected from the group consisting of Groups 7, 8, 9, and 10.

8. The process according to claim 1, wherein said active phase includes a promoter with a content not exceeding 2% by mass.

9. The process according to claim 8, wherein said promoter is selected from the group consisting of rare earth elements and oxides thereof, alkaline earth elements and oxides thereof, and transition metals and oxides thereof.

10. The process according to claim 9, wherein the transition metals are selected from the group consisting of ruthenium, platinum, rhenium, rhodium, iridium, and palladium.

11. The process according to claim 1, wherein said porous support has a specific BET surface area greater than 5 m$^2$/g.

12. The process according to claim 1, wherein said porous support has a microporous surface area greater than 10 m$^2$/g.

13. The process according to claim 12, wherein said porous support has a porous volume in the range of 30 nm and 300 nm measured by mercury intrusion greater than 0.12 cm$^3$/g.

14. The process according to claim 1, wherein said support is in the form of pellets, beads, extrudates, or in the form of a cellular foam.

15. The process according to claim 3, wherein said temperature is at least 400° C.

16. The process according to claim 4, wherein the content of active phase with respect to the total mass of said porous support with its active phase is between 5% and 35%.

17. The process according to claim 4, wherein the content of active phase with respect to the total mass of said porous support with its active phase is 5% and 30%.

18. The process according to claim 11, wherein the specific BET surface area is greater than 30 m$^2$/g.

19. The process according to claim 11, wherein the specific BET surface area is greater than 40 m$^2$/g.

20. The process according to claim 11, wherein the specific BET surface area is greater than 60 m$^2$/g.

21. The process according to claim 1, wherein said molar content of titanium is between 0.5% and 10%.

22. The process according to claim 12, wherein said microporous surface area is greater than 20 m$^2$/g.

23. The process according to claim 13, wherein the porous volume is in the range of greater than 0.15 cm$^3$/g.

24. The process according to claim 13, wherein the porous volume is in the range of greater than 0.20 cm$^3$/g.

* * * * *